United States Patent [19]

Sone et al.

[11] 4,363,306
[45] Dec. 14, 1982

[54] SYSTEM FOR FEEDBACK CONTROL OF AIR/FUEL RATIO IN IC ENGINE HAVING MEANS FOR SUPPLYING CONTROLLED CURRENT TO OXYGEN SENSOR

[75] Inventors: Kohki Sone, Tokyo; Kenji Okamura, Zushi; Toyoaki Nakagawa, Yokohama, all of Japan

[73] Assignee: Nissan Motor Co., Ltd., Yokohama, Japan

[21] Appl. No.: 190,980

[22] Filed: Sep. 26, 1980

[30] Foreign Application Priority Data

Sep. 28, 1979 [JP] Japan ............... 54-134084[U]

[51] Int. Cl.³ .............................................. F02M 7/00
[52] U.S. Cl. .................................. 123/440; 204/195 S
[58] Field of Search .......................... 123/440, 489; 204/195 S; 60/276, 285; 73/23

[56] References Cited

U.S. PATENT DOCUMENTS

| | | |
|---|---|---|
| 3,768,259 | 10/1973 | Carnahan et al. |
| 3,915,135 | 10/1975 | Kushida et al. ............... 204/195 S |
| 3,948,081 | 4/1976 | Wessel et al. |
| 4,107,019 | 8/1978 | Takao et al. |
| 4,112,893 | 9/1978 | Anzai ............... 204/195 S |
| 4,140,085 | 2/1979 | Rabus ............... 123/440 |
| 4,207,159 | 6/1980 | Kimura et al. |
| 4,227,984 | 10/1980 | Dempsey et al. ............... 204/195 S |

FOREIGN PATENT DOCUMENTS

| | | |
|---|---|---|
| 2010793 | 10/1970 | Fed. Rep. of Germany . |
| 2338873 | 2/1975 | Fed. Rep. of Germany . |
| 2709173 | 9/1978 | Fed. Rep. of Germany . |
| 2815141 | 10/1978 | Fed. Rep. of Germany . |
| 2333125 | 6/1977 | France . |
| 2362392 | 3/1978 | France . |
| 2408835 | 6/1979 | France . |
| 54-109523 | 8/1979 | Japan ............... 123/440 |
| 55-40276 | 3/1980 | Japan ............... 123/440 |

*Primary Examiner*—P. S. Lall
*Attorney, Agent, or Firm*—Schwartz, Jeffery, Schwaab, Mack, Blumenthal & Koch

[57] ABSTRACT

A system for feedback control of air/fuel ratio in an internal combustion engine, utilizing an oxygen-sensitive air/fuel ratio detector disposed in an exhaust gas to provide a feedback signal is disclosed. The detector has a flat and microscopically porous solid electrolyte layer with a measurement electrode layer on one side and a reference electrode layer on the other side facing a substrate. The control system includes a current supplying circuit to force a DC current to flow in the solid electrolyte layer between the two electrode layers to cause migration of oxygen ions through the solid electrolyte layer from the measurement electrode toward the reference electrode to thereby establish a reference oxygen partial pressure at the interface between the reference electrode layer and the solid electrolyte layer. To preclude an undesirably great rise of this reference oxygen partial pressure in the case of a large increase in the amount of oxygen in the exhaust gas resulting from interruption, or great reduction, of the feed of fuel to the operating engine, the control system comprises sensor means to detect the existence of such a condition and means for temporarily decreasing the intensity of the current being supplied to the air/fuel ratio detector.

6 Claims, 4 Drawing Figures

SYSTEM FOR FEEDBACK CONTROL OF AIR/FUEL RATIO IN IC ENGINE HAVING MEANS FOR SUPPLYING CONTROLLED CURRENT TO OXYGEN SENSOR

BACKGROUND OF THE INVENTION

This invention relates to a system for the feedback control of the air/fuel mixture ratio for an internal combustion engine, which system includes an air/fuel ratio detector having an oxygen-sensitive element of the oxygen concentration cell type operated with a DC current to establish a reference oxygen partial pressure in the element, and more particularly to an improved current control means for controlling the supply of current to the oxygen-sensitive element.

In recent internal combustion engines and particularly in automotive engines, it has become popular to control the air/fuel mixture ratio precisely to a predetermined optimal value by performing feedback control with the object of improving the efficiency of the engine and reducing the emission of noxious or harmful substances contained in exhaust gases.

For example, in an automotive engine system which includes a catalytic converter positioned in the exhaust passage and containing a three-way catalyst, that can catalyze both the reduction of nitrogen oxides and oxidation of carbon monoxide and unburned hydrocarbons, it is desirable to control the air/fuel mixture ratio to a stoichiometric ratio since the catalyst exhibits its highest conversion efficiencies in an exhaust gas produced by the combustion of a stoichiometric air-fuel mixture, and also because the employment of a stoichiometric mixture ratio enhances the mechanical and thermal efficiency of the engine. It is known to feedback control the air/fuel ratio in an engine system by using a sort of oxygen sensor, installed in the exhaust passage upstream of the catalytic converter, as a device that provides an electrical feedback signal indicative of the air/fuel ratio of the air-fuel mixture actually supplied to the engine. Based on this feedback signal, a control circuit commands a fuel-supply apparatus, such as electronically controlled fuel injection valves, to control the rate of fuel feed to the engine so as to nullify or minimize deviations of the actual air/fuel ratio from the intended stoichiometric ratio.

Usually the above mentioned oxygen sensor is of an oxygen concentration cell type utilizing an oxygen ion conductive solid electrolyte, such as zirconia stabilized with calcia, and conventionally the sensor comprises a solid electrolyte layer in the shape of a tube closed at one end, a measurement electrode layer porously formed on the outer side of the solid electrolyte tube and a reference electrode layer formed on the inner side of the tube. When there is a difference in oxygen partial pressure between the reference electrode side and measurement electrode side of the solid electrolyte tube, this sensor generates an electromotive force between the two electrode layers. As an air/fuel ratio detector for the above mentioned purpose, the measurement electrode is exposed to an engine exhaust gas while the reference electrode on the inside is exposed to atmospheric air utilized as the source of a reference oxygen partial pressure. In this state, the magnitude of the electromotive force generated by this sensor exhibits a great and sharp change between a maximally high level and a very low level each time the air/fuel ratio of a mixture supplied to the engine changes across the stoichiometric ratio. Accordingly, it is possible to produce a fuel feed rate control signal based on the result of a comparison of the output of the oxygen sensor with a reference voltage which has been set at the middle of the high and low levels of the sensor output.

However, this type of oxygen sensor has disadvantages such as the significant temperature dependence of its output characteristics, the necessity of using a reference gas such as air, the difficulties in reducing the size and its insufficient mechanical strength.

To eliminate such disadvantages of conventional oxygen sensor, U.S. Pat. No. 4,207,159 discloses an advanced device comprising an oxygen-sensitive element having an oxygen concentration cell is comprising of a flat and microscopically porous layer of solid electrolyte, a measurement electrode layer porously formed on one side of the solid electrolyte layer and a reference electrode layer formed on the other side on a base plate or substrate such that the reference electrode layer is sandwiched between the substrate and the solid electrolyte layer and macroscopically shielded from the environmental atmosphere. Each of the three layers on the substrate can be formed as a thin, film-like layer. This device does not use any reference gas. Instead, a DC power supply means is connected to the oxygen-sensitive element so as to force a constant DC current (e.g. of a current intensity of about 10 $\mu$A) to flow through the solid electrolyte layer between the two electrode layers to thereby cause migration of oxygen ions through the solid electrolyte layer in a selected direction and, as a consequence, establish a reference oxygen partial pressure at the interface between the solid electrolyte layer and the reference electrode layer, while the measurement electrode layer is made to contact an engine exhaust gas. Where the current is formed to flow through the solid electrolyte layer from the reference electrode layer toward the measurement electrode layer, there occur ionization of oxygen contained in the exhaust gas at the measurement electrode and migration of negatively charged oxygen ions through the solid electrolyte layer toward the reference electrode. The rate of supply of oxygen in the form of ions to the reference electrode is primarily determined by the intensity of the current. The oxygen ions arriving at the reference electrode layer are deprived of electrons and turn into oxygen molecules which result in accumulation of gaseous oxygen on the reference electrode side of the concentration cell. However, a portion of the accumulated oxygen molecules diffuse outwardly through microscopical gas passages in the solid electrolyte layer. Therefore, it is possible to maintain a constant and relatively high oxygen partial pressure which can serve as a reference oxygen partial pressure at the interface between the reference electrode layer and the solid electrolyte layer by the employment of an appropriate current intensity with due consideration of the microscopical structure and activity of the solid electrolyte layer. Between the reference and measurement electrode layers of the oxygen-sensitive element then is generated an electromotive force, the magnitude of which is related to the composition of the exhaust gas and the air/fuel ratio of the mixture from which the exhaust gas is produced. The oxygen-sensitive element may be operated by forcing a current to flow therein from the measurement electrode layer toward the reference electrode layer. In this case a constant and relatively low oxygen partial pressure can be maintained at the interface between the reference electrode layer and the solid electrolyte layer.

To supply a DC current of an accurate and constant intensity, use is made of a constant current supply circuit including conventional electronic control means.

Sensors of the type disclosed in U.S. Pat. No. 4,207,159 has advantages over prior sensors in that they require no reference gas, they can be produced a very small size and exhibit good resistance to mechanical shocks and vibrations.

In performing feedback control of the air/fuel ratio in the engine system discussed above, utilizing an air/fuel ratio detector according to U.S. Pat. No. 4,207,159 (and also in the case of using a conventional oxygen sensor), it is usual to interrupt the feed of fuel to the engine under certain operating conditions of the engine such as an abrupt deceleration condition, with a view to avoiding wasteful consumption of fuel. Under such conditions, there occur a considerable augmentation of oxygen concentration in the exhaust gas and lowering of the temperature of the exhaust gas and of the oxygen-sensitive element, with a resultant tendency of the solid electrolyte layer in the element lowering its activity. This results in an increase in the amount of oxygen ions supplied to the reference electrode layer relative to the amount of oxygen molecules diffusing outwardly through the pores in the solid electrolyte layer, even though the intensity of the DC current supplied to the element is kept unchanged. Consequently, the magnitude of an oxygen partial pressure on the reference electrode side becomes far greater than the initially intended value. When this oxygen partial pressure continues to rise beyond a certain critical level, there is a strong possibility of breakage of the oxygen-sensitive element which is comprises very thin layers. A similar tendency is apparent when the air/fuel ratio becomes exceedingly high, even though the feed of fuel is not completely interrupted and/or when the exhaust gas temperature becomes very low during operation of the oxygen-sensitive element.

SUMMARY OF THE INVENTION

It is an object of the present invention to provide a system for feedback control of air/fuel ratio in an internal combustion engine, which system utilizes an oxygen-sensitive air/fuel ratio detector of the type disclosed in U.S. Pat. No. 4,207,159 disposed in an exhaust passage and comprises a supplementary control loop to preclude an undesirably great rise of a reference oxygen partial pressure established in the air/fuel ratio detector when the feed of fuel to the operating engine is interrupted, or when the fuel feed rate is so decreased as to bring about an exceedingly high air/fuel ratio, and/or when the exhaust gas temperature is very low.

In the present invention it is a primary matter object to preclude an undesirably large increase in the magnitude of the reference oxygen partial pressure in the air/fuel ratio detector during any interruption of the fuel feed to an operating engine. Moreover, in a control system according to the invention, it is an object of the present invention to preclude similarly undesirable rising tendencies of the reference oxygen partial pressure under certain operating conditions other than a fuel-cut condition.

A feedback control system according to the invention comprises an electrically controllable fuel supply means provided in the intake system of an internal combustion engine; an air/fuel ratio detector which is disposed in an exhaust passage of the engine and which has an oxygen-sensitive element of a concentration cell type comprising a substrate, a microscopically porous reference electrode layer formed on the substrate, a microscopically porous layer of an oxygen ion conductive solid electrolyte formed on the substrate so as to cover the reference electrode layer substantially entirely and a microscopically porous measurement electrode layer formed on the solid electrolyte layer; operating condition detecting means for detecting at least one of (i) an exceedingly high air/fuel ratio condition where the air/fuel ratio in the engine is above an upper boundary of an expected range of fluctuations of air/fuel ratio under feedback control and practically infinite in the extreme case and (ii) an exceedingly low exhaust temperature condition where the temperature of the exhaust gas in the exhaust passage is below a lower boundary of a temperature range for effective function of the oxygen-sensitive element and generating a command signal indicative of the existence of the detected condition; and control means for providing a control signal to the fuel supply means to control the rate of fuel feed to the engine so as to maintain a predetermined air/fuel ratio by utilizing the output of the air/fuel ratio detector as a feedback signal. This control means includes a circuit to force a DC current of a predetermined intensity to flow through the solid electrolyte layer of the oxygen-sensitive element from the reference electrode layer toward the measurement electrode layer to cause migration of oxygen ions through the solid electrolyte layer from the measurement electrode layer toward the reference electrode layer to thereby establish a reference oxygen partial pressure at the interface between the reference electrode layer and the solid electrolyte layer. Furthermore, this control means includes a current-intensity altering means for temporarily decreasing the intensity of the DC current being supplied to the oxygen-sensitive element from the aforementioned predetermined intensity while the operating condition detecting means continues to generate the command signal for thereby precluding an undesirably large rise in the reference oxygen partial pressure.

For example, the current supplying circuit may have a comparator which produces a current-intensity regulating output based upon the result of a comparison between the actual intensity of the current being supplied to the oxygen-sensitive element and a reference signal produced by applying a constant voltage to a voltage-dividing resistance. The above stated current-intensity altering means has the function of varying the effective value of this voltage-dividing resistance in response to the command signal.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

Figure 1:
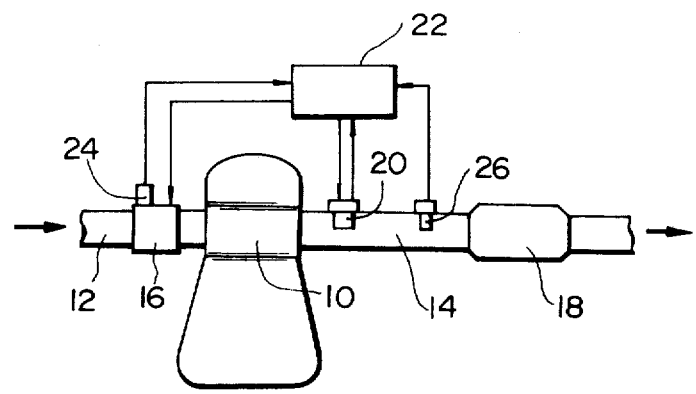
FIG. 1 is a diagrammatic presentation of an internal combustion engine system including an air/fuel ratio control system with which the present invention is concerned.

In FIG. 1, reference numeral 10 indicates an internal combustion engine, which may be an automotive engine, provided with an induction passage 12 and an exhaust passage 14. Indicated at 16 is an electrically or electronically controlled fuel-supplying apparatus such as electronically controlled fuel injection valves. A catalytic converter 18 occupies a section of the exhaust passage 14 and contains therein a conventional three-way catalyst.

The fuel-supply apparatus 16 is feedback controlled to supply a constant stoichiometric air-fuel mixture to the engine 10 during its normal operation to thereby allow the three-way catalyst in the converter 18 to exhibit its best conversion efficiencies. For this purpose, an air/fuel ratio detector 20 (which is an oxygen sensor in principle) is disposed in the exhaust passage 14 at a section upstream of the catalytic converter 18. An electronic control unit 22 receives the output of the air/fuel ratio sensor 20 and provides a control signal to the fuel-supply apparatus 16 based on the magnitude of a deviation of the actual air/fuel ratio indicated by the output of the sensor 20 from the stoichiometric air/fuel ratio. The control unit 22 includes a circuit to supply a constant DC current to the air/fuel ratio detector 20.

According to the present invention, this current supply circuit has the function of temporarily decreasing the intensity of its output if the engine 10 is operated under certain conditions, for example where the supply of fuel from the apparatus 16 is interrupted or so greatly reduced as to cause a great rise of deviation of the air/fuel ratio from the stoichiometric ratio toward the lean side and/or where the exhaust gas temperature becomes very low. To detect such conditions, the control system of FIG. 1 includes an operating condition sensor 24 and/or an exhaust gas temperature sensor 26. The output of sensors 24 and/or 26 are fed into the control unit 22. The current-decreasing function and the sensor 24 will later be described more in detail.

Figure 2:
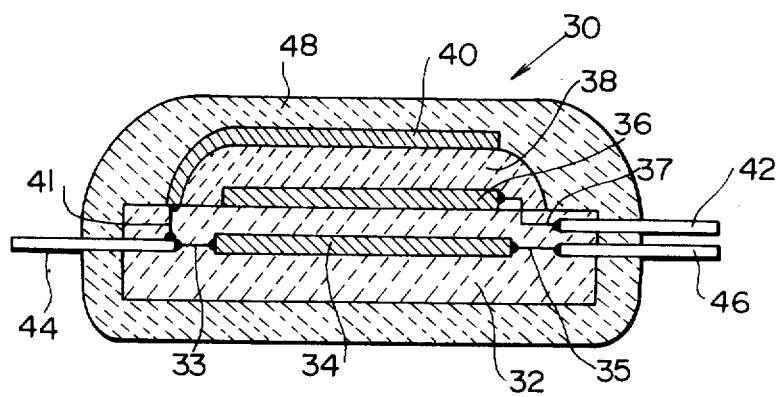
FIG. 2 is a schematic and sectional view of an oxygen-sensitive element of an air/fuel ratio detector employed in the present invention.

FIG. 2 shows an exemplary construction of an oxygen-sensitive element 30 of the oxygen sensor employed as the air/fuel ratio detector 20 in the system of FIG. 1. This element 30 is of the type disclosed in the aforementioned U.S. Pat. No. 4,207,159.

A structurally basic member of this oxygen-sensitive element 30 is a substrate 32 made of a ceramic material such as alumina. Usually a heater element 34 is embedded in the alumina substrate 32 because the oxygen-sensitive element 30 exhibits its proper function only when maintained at sufficiently elevated temperatures, e.g. at temperatures above about 500° C. In practice, the alumina substrate 32 is obtained by face-to-face bonding of two alumina sheets, one of which is provided with the heater element 34 in the form of, for example, a platinum layer of a suitable pattern.

An electrode layer 36 is formed on one side of the substrate 32. On that same side, a layer 38 of an oxygen ion conductive solid electrolyte such as $ZrO_2$ stabilized with CaO or $Y_2O_3$ is formed so as to cover substantially the entire area of the electrode layer 36. Another electrode layer 40 is formed on the outer surface of the solid electrolyte layer 38. Platinum is a typical example of electronically conductive materials for the inner and outer electrode layers 36 and 40. Each of these three layers 36, 38, 40 is a thin, film-like layer (though a "thick layer" in the sense of the current electronic technology), so that the total thickness of these three layers is only on the order of about 20 $\mu m$ by way of example. Macroscopically the inner electrode layer 36 is completely shielded from an environmental atmosphere by the substrate 32 and the solid electrolyte layer 38. However, both the solid electrolyte layer 38 and the outer electrode layer 40 (the inner electrode layer 36 too) are microscopically porous and permeable to gas molecules. As is known, these three layers 36, 38, 40 constitute an oxygen concentration cell which generates an electromotive force when there is a difference in oxygen partial pressure between the inner electrode side and the outer electrode side of the solid electrolyte layer 38. This element 30 is so designed to establish a reference oxygen partial pressure at the interface between the inner electrode layer 36 and the solid electrolyte layer 38 by externally applying a DC current to the concentration cell to flow through the solid electrode layer 38 between the two electrode layers 36 and 40, while the outer electrode layer 40 is exposed to a gas subject to measurement, such as an exhaust gas flowing through the exhaust passage 14 in FIG. 1. Accordingly, the inner electrode 36 will be referred to as reference electrode layer and the outer electrode layer 40 as measurement electrode layer.

Attached to the substrate 32 are three lead terminals 42, 44 and 46. The reference electrode layer 36 is electrically conncted to the lead terminal 42 either directly or via a lead 37, and the measurement electrode layer 40 is electrically connected to the lead terminal 44 either directly or via a lead 41. The heater element 34 is connected to the lead terminals 44 and 46 either directly or via leads 33, 35, so that the lead terminal 44 serves as a ground terminal common to the heater 34 and the oxygen concentration cell of the element 30. The aforementioned DC current is applied to the oxygen concentration cell to flow from the lead terminal 42 to the ground lead terminal 44 through the solid electrolyte layer 38, and the electromotive force generated by the oxygen concentration cell is measured between these two lead terminals 42 and 44.

As a practical device, the oxygen-sensitive element 30 is substantially entirely covered with a gas permeably porous protective layer 48 of a ceramic material, such as alumina, spinel or calcium zirconate.

The principle of the function of this oxygen-sensitive element 30 has already been described in this specification.

Figure 3:
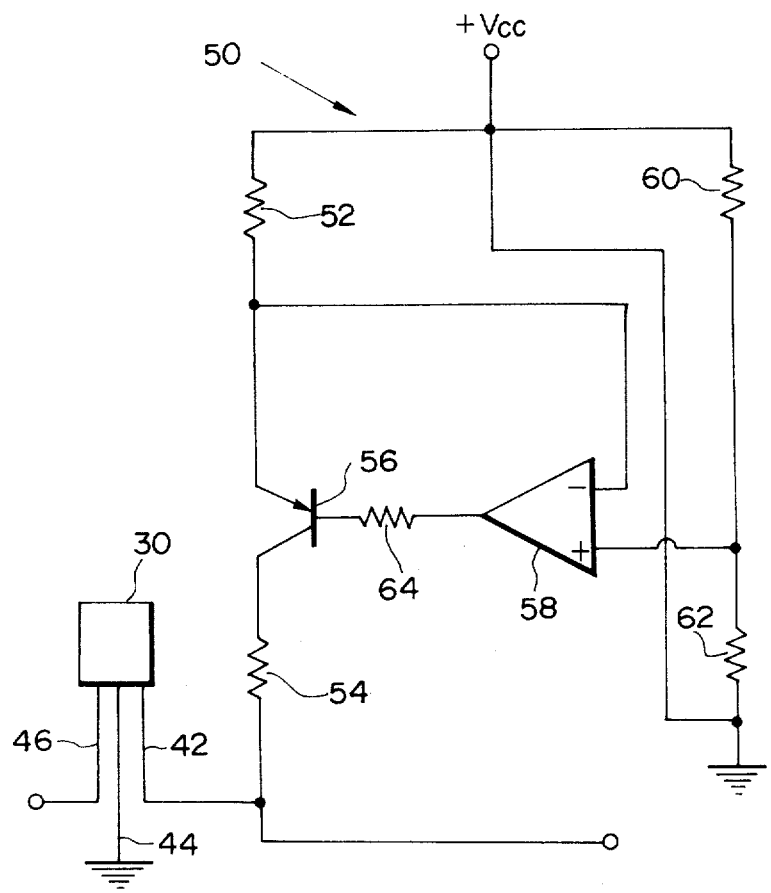
FIG. 3 is a circuit diagram showing a conventional circuit to supply a constant DC current to the oxygen-sensitive element of FIG. 2 in the system of FIG. 1.

FIG. 3 shows a constant current supplying circuit 50 hitherto used as part of a control unit corresponding to the unit 22 in FIG. 1 to supply a DC current of a constant intensity to the oxygen-sensitive element 30 of the sensor 20.

This circuit 50 has resistors 52 and 54 connected in series with the interposed transistor 56 such that a DC current of a predetermined intensity, originating from the source voltage $V_{cc}$, flows into the oxygen-sensitive element 30 via the lead terminal 42 through the resistor 52, emitter-collector circuit of the transistor 56 and the resistor 54. There is a comparator 58 with its negative input terminal connected to a junction between the resistor 52 and the transistor 56, so that the intensity of the current supplied to the oxygen-sensitive element 30 is monitored by the comparator 58 as the magnitude of a voltage drop across the resistor 52. The source voltage $V_{cc}$ is also applied to a voltage divider consisting of two series-connected resistors 60 and 62, and the positive input terminal of the comparator 58 is connected to a junction between these two resistors 60 and 62, while the output terminal of the comparator 58 is connected to the base of the transistor 56 via a resistor 64. The resistors 60 and 62 have resistance values such that the magnitude of a voltage drop across the resistor 60 serves as a reference value corresponding to the predetermined intensity of the DC current supplied to the oxygen-sensitive element 30. Based on the result of a comparison between the two voltage drop values respectively put into the negative and positive input terminals, the comparator 58 regulates the base current of the transistor 56. That is, when the magnitude of the voltage drop attributed to the resistor 52 is greater than the reference value, meaning that the intensity of the current to the oxygen-sensitive element 30 is smaller than the predetermined intensity, the output of the comparator 58 causes the base current of the transistor 56 to increase to thereby increase the current to the oxygen-sensitive element 30 up to the predetermined intensity. In the contrary case, the output of the comparator 58 causes the base current of the transistor 56 to decrease to thereby decrease the current intensity for the oxygen-sensitive element 30 to the predetermined intensity. Thus, a constant DC current can be kept flowing in the oxygen-sensitive element 30 even when, for example, a change occurs in the internal resistance of the element 30.

Figure 4:
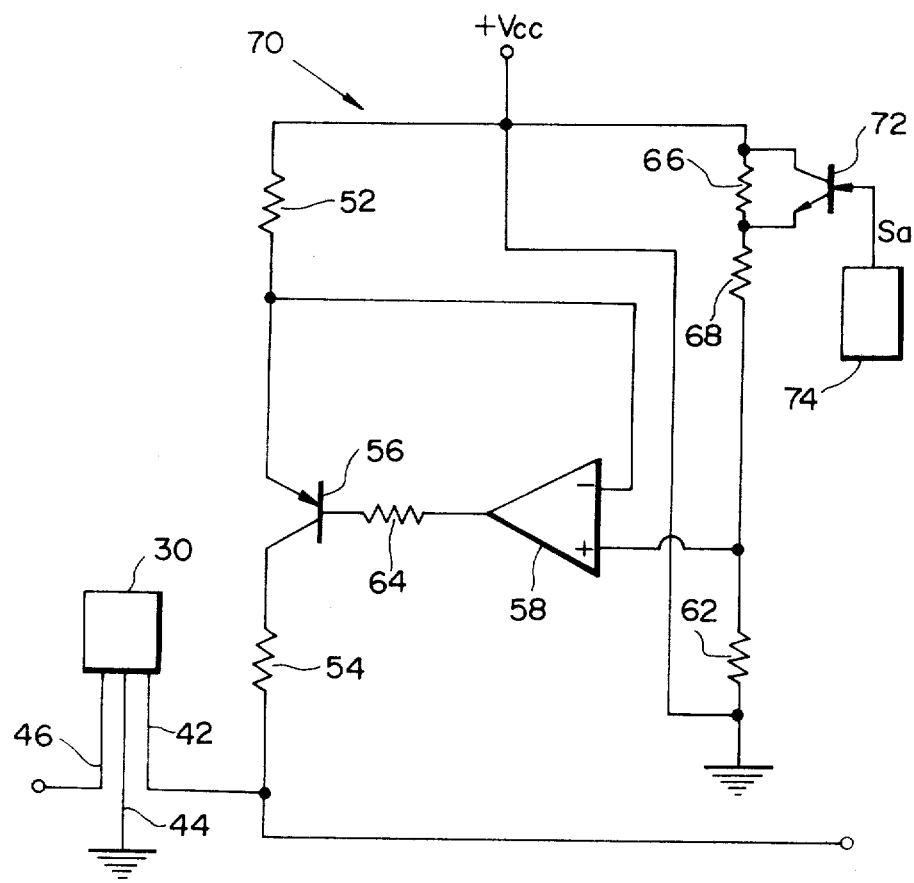
FIG. 4 is a circuit diagram showing a current supply circuit which is fundamentally similar to the circuit of FIG. 3 and modified in accordance with the present invention.

FIG. 4 shows an example of a current supplying circuit according to the invention, which is incorporated in the control unit 22 of FIG. 1. This circuit 70 is fundamentally similar to the circuit 50 of FIG. 3. As the sole modification, the circuit 70 has two series-connected resistors 66 and 68 in place of the voltage-dividing resistor 60 in the circuit 50 of FIG. 3 and a switching transistor 72 of which the collector-emitter circuit is connected in parallel with the resistor 66. The base of this transistor 72 is connected with sensor means 74 which corresponds to the operating conditions sensor 24 and/or the exhaust gas temperature sensor 26 in FIG. 1, possibly via a signal-treating circuit (not shown). The sum of the resistances of the two resistors 66 and 68 corresponds to the resistance of the resistor 60 in FIG. 3, and the transistor 72 is kept in the nonconducting state during performance of feedback control of the air/fuel ratio. Accordingly the magnitude of the voltage drop attributed to the resistors 66 and 68 is taken as the reference value in the function of the comparator 58 to supply a constant current to the oxygen-sensitive element 30 in the same way as described hereinbefore with respect to the circuit 50 of FIG. 3.

The sensor means 74 provides a signal $S_a$, which causes the transistor 72 to become conducting, when this sensor means 74 detects that the engine 10 is operating under such a condition that the magnitude of the reference oxygen partial pressure in the oxygen-sensitive element 30 will become undesirably great if the supply of a current of the predetermined intensity is continued.

More precisely, the signal $S_a$ may be provided when the sensor means 74 detects that the feed of fuel to the engine 10 is interrupted, or the rate of fuel feed is so reduced that the resultant air/fuel ratio becomes distinctly higher than the upper boundary of an expected range of fluctuations of air/fuel ratio under feedback control, and/or that the exhaust gas temperature is below a predetermined lower boundary. Numerically, an expected range of fluctuations of air/fuel ratio under feedback control, i.e. the scale of control error, is usually on the order of about ±0.25 (in terms of air/fuel ratio by weight) with respect to the target value of the control, such as the stoichiometric air/fuel ratio 14.7 in a gasoline engine, and on the order of about ±0.5 in the largest case, and the lower boundary of the exhaust gas temperature is usually set within the range from about on the order of 250° C. to 300° C. The parameters of the engine operating conditions subject to detection by the sensor means 74 are selected from the appearance of a fuel-cut signal, the state of fuel injection control signal such as the durations of individual pulses of a pulse signal, the state of function of fuel injection valves, the appearance of a feedback control release signal, and a combination of at least two of the magnitude of intake vacuum, rate of air intake, degree of throttle opening and rotational speed of the engine, aside from the temperature of exhaust gas. In addition, the detector may detect an unintentional condition wherein the fuel-feed control signal continues to imply a decrease the rate of fuel feed for an unduly long period of time. In practice, the sensor means 74 and/or the aforementioned signal-treating circuit are designed such that the signal $S_a$ is generated only when a fuel-cut condition, or a very high air/fuel ratio condition, and/or a very low exhaust temperature condition is maintained for a predetermined zength of time.

When the transistor 72 becomes conducting in response to the signal $S_a$, the resistor 66 essentially becomes short-circuited so that the magnitude of the voltage drop put into the comparator 58 as the reference value becomes higher. Therefore the output of the comparator 58 varies to decrease the base current of the transistor 56 until the current supplied to the oxygen-sensitive element 30 decreases to such an extent that the magnitude of voltage drop across the fixed resistor 52 decreases and corresponds with the decreased reference value.

The decrease in the intensity of the current flowing through the solid electrolyte layer 38 of the oxygen-sensitive element 30 results in lowering the rate of supply of oxygen in the form of ions from the measurement electrode layer 40 to the reference electrode layer 36. Therefore, an undesirably great rise in the oxygen partial pressure at the interface between the reference electrode layer 38 and the possibility of resultant breakage of the oxygen-sensitive element 30 may be effectively precluded, and the service life of the element 30 will be prolonged.

Upon disappearance of the signal $S_a$ the transistor 72 resumes the nonconducting state, so that the intensity of the current being supplied to the oxygen-sensitive element 30 increases to the initially set value.

The oxygen-sensitive element 30 of FIG. 2 can be used also for detection of a non-stoichiometric air/fuel ratio, either higher or lower than the stoichiometric ratio, by determining the intensity of the DC current flowing in the solid electrolyte layer 38. In the above described embodiment of the present invention, the aim of feedback control of air/fuel ratio was a stoichiometric ratio. However, the present invention is applicable also to analogous air/fuel ratio control systems designed to maintain a non-stoichiometric air/fuel ratio by using an oxygen-sensitive element of the type as shown in FIG. 2.

The oxygen-sensitive element 30 of FIG. 2 may also be operated by forcing a constant DC current to flow in the solid electrolyte layer 38 from the measurement electrode layer 40 toward the reference electrode layer 36. The fundamental concept of the present invention remains applicable when the element 30 is operated with the supply of a current in that direction. In such a case, the herein described characteristics of the current intensity control function of the current supplying circuit of the invention should be reversed.

The foregoing description of preferred embodiments of the invention have been presented for purposes of illustration and description. They are not intended to be exhaustive or to limit the invention to the precise form disclosd, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for feedback control of the air/fuel ratio of an air-fuel mixture supplied to an internal combustion engine, the control system comprising:
   an electrically controllable fuel supply means provided in the intake system of the engine;
   an air/fuel ratio detector disposed in an exhaust passage for the engine and having an oxygen-sensitive element of a concentration cell type comprising a substrate, a microscopically porous reference electrode layer formed on the substrate, a microscopically porous layer of an oxygen ion conductive solid electrolyte formed on the substrate so as to cover the reference electrode layer substantially entirely and a microscopically porous measurement electrode layer formed on the solid electrolyte layer;
   operating condition detecting means for detecting at least one of (i) an exceedingly high air/fuel ratio condition where the air/fuel ratio is above an upper boundary of an expected range of fluctuations of air/fuel ratio under feedback control and (ii) an exceedingly low exhaust temperature condition where the temperature of the exhaust gas in the exhaust passage is below a lower boundary of a temperature range for effective function of the oxygen-sensitive element, and for generating a command signal indicative of the existence of the detected condition; and
   control means for providing a control signal to the fuel supplying means to control the rate of fuel feed to the engine so as to maintain a predetermined air/fuel ratio by utilizing the output of the air/fuel ratio detector as a feedback signal, the control means including a circuit for providing a DC current of a predetermined intensity to flow through the solid electrolyte layer of the oxygen-sensitive element to thereby establish a reference oxygen partial pressure at the interface between the reference electrode layer and the solid electrolyte layer, the control means further comprising a current-intensity altering means for decreasing the intensity of said DC current from said predetermined intensity while the operating condition detecting means continues to generate said command signal whereby an undesirable rise of said reference oxygen partial pressure is precluded.

2. A system according to claim 1, wherein the current supplying circuit comprises a comparator which produces a current-intensity regulating output based on the result of a comparison between actual intensity of said DC current and a reference signal produced by applying a constant voltage to a voltage-dividing resistance, the current-intensity altering means comprising means for varying the effective value of said voltage-dividing resistance in response to said command signal.

3. A system according to claim 2, wherein said means for varying the effective value of said voltage-dividing resistance comprises a switching transistor which is arranged so as to short-circuit a part of said voltage-dividing resistance in response to said command signal.

4. A system according to claims 1 or 2, wherein the operating condition detecting means detects said exceedingly high air/fuel ratio condition by detecting at least one of (a) appearance of a signal commanding interruption of the feed of fuel, (b) actual state of the function of the fuel supply means, (c) actual state of said control signal, (d) a combination of at least two of the magnitude of intake vacuum, rate of air intake, degree of throttle opening and rotational speed of the engine.

5. A system according to claims 1 or 2, wherein said predetermined air/fuel ratio is a stoichiometric air/fuel ratio.

6. A system according to claims 1 or 2, wherein the oxygen-sensitive element further comprises a heater element attached to said substrate.

* * * * *